United States Patent
Ren et al.

(10) Patent No.: US 11,426,496 B2
(45) Date of Patent: Aug. 30, 2022

(54) METHOD FOR PREPARING ANTI-BACTERIAL SURFACE ON MEDICAL MATERIAL SURFACE

(71) Applicant: South China University of Technology, Guangzhou (CN)

(72) Inventors: Li Ren, Guangzhou (CN); Lin Wang, Guangzhou (CN); Jingcai He, Guangzhou (CN); Yingjun Wang, Guangzhou (CN)

(73) Assignee: South China University of Technology

( * ) Notice: Subject to any disclaimer, the term of this patent is extended or adjusted under 35 U.S.C. 154(b) by 713 days.

(21) Appl. No.: 16/475,196

(22) PCT Filed: Nov. 14, 2017

(86) PCT No.: PCT/CN2017/110895
§ 371 (c)(1),
(2) Date: Jul. 1, 2019

(87) PCT Pub. No.: WO2018/126796
PCT Pub. Date: Jul. 12, 2018

(65) Prior Publication Data
US 2019/0328939 A1    Oct. 31, 2019

(30) Foreign Application Priority Data
Jan. 5, 2017   (CN) .......................... 201710006283.4

(51) Int. Cl.
*A61L 31/16*   (2006.01)
*A61L 31/10*   (2006.01)
(Continued)

(52) U.S. Cl.
CPC .............. *A61L 31/16* (2013.01); *A61L 31/10* (2013.01); *C04B 41/4533* (2013.01);
(Continued)

(58) Field of Classification Search
None
See application file for complete search history.

(56) References Cited

FOREIGN PATENT DOCUMENTS

| CN | 1775313 A | 5/2006 |
| CN | 1960736 A | 5/2007 |

(Continued)

OTHER PUBLICATIONS

Li et al., "Construction of a Highly Biocompatible Antibacterial Iron-Based Implant Based on Multiple Skins", 2014, China Academic Journal Electronic Publishing House, 4 pages.

*Primary Examiner* — Melissa S Mercier
(74) *Attorney, Agent, or Firm* — The Webb Law Firm (57) ABSTRACT

The present invention discloses a method for preparing an anti-bacterial surface on a medical material surface, including the steps of: (1) conducting chemical graft of amino silane after performing oxygen plasma pretreatment to the medical material surface and then reacting the medical material with the amino silane surface with an acyl compound; (2) placing the medical material with an initiator-modified surface into an anti-adhesion monomer aqueous solution for a graft polymerization reaction; (3) placing the medical material with an anti-adhesion polymer brush-modified surface into an azide compound-containing dimethylformamide solution; and (4) placing the medical material with an azide surface into an anti-bacterial agent click solution for a click reaction, obtaining an anti-adhesion polymer layer—and anti-bacterial agent layer-comodified anti-bacterial surface. The method prevents mutual interference of the anti-adhesion ability and bactericidal ability, and has good long-acting anti-bacterial performance.

10 Claims, 7 Drawing Sheets

Specification includes a Sequence Listing.

(51) Int. Cl.
*C08F 292/00* (2006.01)
*C04B 41/45* (2006.01)
*C23C 16/455* (2006.01)

(52) U.S. Cl.
CPC ...... *C08F 292/00* (2013.01); *C23C 16/45536* (2013.01); *A61L 2300/252* (2013.01); *A61L 2300/404* (2013.01); *A61L 2400/18* (2013.01); *C08F 2438/01* (2013.01)

(56) References Cited

FOREIGN PATENT DOCUMENTS

| | | | |
|---|---|---|---|
| CN | 101787136 A | | 7/2010 |
| CN | 102216376 A | | 10/2011 |
| CN | 102911378 A | | 2/2013 |
| CN | 104710644 A | * | 6/2015 |
| CN | 105601976 A | | 5/2016 |
| CN | 105949322 A | | 9/2016 |
| CN | 106902396 A | | 6/2017 |
| CN | 104710644 B | | 9/2017 |
| FR | 2905271 A1 | | 3/2008 |
| WO | 9219289 A1 | | 11/1992 |

\* cited by examiner

SEQUENCE LISTING

```
<160> NUMBER OF SEQ ID NOS: 4

<210> SEQ ID NO 1
<211> LENGTH: 30
<212> TYPE: PRT
<213> ORGANISM: Artificial Sequence
<220> FEATURE:
<223> OTHER INFORMATION: Peptide

<400> SEQUENCE: 1

Pro Arg Ala Leu Tyr Ser Ala Arg Gly Thr Arg Pro Thr Arg Pro Leu
1               5                   10                  15

Tyr Ser Thr Arg Pro Thr Arg Pro Ala Arg Gly Ala Arg Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Peptide

<400> SEQUENCE: 2

Pro Arg Ala Ala Arg Gly Ala Arg Gly Thr Arg Pro Thr Arg Pro Leu
1               5                   10                  15

Tyr Ser Thr Arg Pro Thr Arg Pro Ala Arg Gly Leu Tyr Ser
            20                  25                  30

<210> SEQ ID NO 3
<211> LENGTH: 10
<212> TYPE: PRT
<213> ORGANISM: Artificial Sequence
<220> FEATURE:
<223> OTHER INFORMATION: antimicrobial peptide
<220> FEATURE:
<221> NAME/KEY: MISC_FEATURE
<222> LOCATION: (1)..(1)
<223> OTHER INFORMATION: X is Pra

<400> SEQUENCE: 3

Xaa Lys Arg Trp Trp Lys Trp Trp Arg Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: antimicrobial peptide
<220> FEATURE:
<221> NAME/KEY: MISC_FEATURE
<222> LOCATION: (1)..(1)
<223> OTHER INFORMATION: X is Pra

<400> SEQUENCE: 4

Xaa Arg Arg Trp Trp Lys Trp Trp Arg Lys
1               5                   10
```

METHOD FOR PREPARING ANTI-BACTERIAL SURFACE ON MEDICAL MATERIAL SURFACE

CROSS-REFERENCE TO RELATED APPLICATIONS

This application is the United States national phase of International Application No. PCT/CN2017/110895 filed Nov. 14, 2017, and claims priority to Chinese Patent Application No. 201710006283.4 filed Jan. 5, 2017, the disclosures of each of which are hereby incorporated by reference in their entireties.

The Sequence Listing associated with this application is filed in electronic format via EFS-Web and is hereby incorporated by reference into the specification in its entirety. The name of the text file containing the Sequence Listing is 8692_1904347_ST25.txt. The size of the text file is 1,629 bytes, and the text file was created on Jun. 21, 2019.

BACKGROUND OF THE INVENTION

Field of the Invention

The present invention relates to a medical material, and more particularly to a method for preparing an anti-bacterial surface on a medical material surface.

Description of Related Art

Our health is threatened by some microbes, and anti-bacterial materials become very important in daily lives. With the improvement of social health awareness, the application of implant materials has become more and more widespread, and the problem of implant infection caused by bacteria has been paid more and more attention. Although the aseptic treatment of materials and the use of preoperative antibiotics can reduce the incidence of such infections, 4%-6% of patients still suffer from implant failure due to bacterial infection at the initial stage of implantation, bringing patients great pain and financial burden. In China, the clinical incidence of such infections is as high as 15%. Therefore, the implant material not only requires good biocompatibility, but also has a necessary anti-bacterial ability. Silicon materials are widely used in construction of surface modification models due to good surface regularity and low specific adsorption.

The problem that bacterial infections of an implant material is difficult to cure determines that for bacterial infections of an implant, measures putting more emphasis on prevention than treatment on the bacterial infection of the implant should be taken. Namely, the implant material has excellent tissue compatibility and biocompatibility, and also has excellent anti-bacterial performance. In order to improve the anti-bacterial performance of the implant material, it is an effective method to perform surface modification on the material and construct an anti-bacterial surface on the surface thereof by using various anti-bacterial agents. Currently, the anti-bacterial agents commonly used in clinic include ionic anti-bacterial agents, such as silver sulfadiazine; and antibiotic anti-bacterial agents, such as tetracycline and vancomycin. Although the materials added with these anti-bacterial agents have strong anti-bacterial performance, the cytotoxicity of silver ions is relatively large, and antibiotics tend to make bacteria resistant to antibiotics. Drug-resistant bacteria have become a major clinical challenge. These problems have made certain limitations on the clinical application of these anti-bacterial agents, and a new type of anti-bacterial agent is urgently needed.

SUMMARY OF THE INVENTION

In order to overcome the problems in the prior art that an anti-adhesion polymer layer and an anti-bacterial agent are introduced on the surface of a medical material, resulting in the mutual interference of the anti-adhesion ability and bactericidal ability to affect the anti-bacterial ability of the surface, and the polypeptide anti-bacterial agent itself is unstable, the object of the present invention is to provide a method for preparing an anti-bacterial surface on a medical material surface, which avoids mutual interference of performance, and improves the problem of enzymatic degradation of the anti-bacterial agent in the body, obtaining more excellent long-acting anti-bacterial performance.

The objective of the present invention is realized by the following technical solutions:

The present invention discloses a method for preparing an anti-bacterial surface on a medical material surface, comprising the steps of:

(1) conducting chemical graft of amino silane after performing oxygen plasma pretreatment to the medical material surface and then reacting the medical material with an amino silane-grafted surface with an acyl compound, obtaining a medical material with an initiator-modified surface for atom transfer radical polymerization;

(2) placing the medical material with the initiator-modified surface obtained by step (1) into an mixed solution for anti-adhesion monomer radical polymerization for a graft polymerization reaction, obtaining a medical material with an anti-adhesion polymer brush-modified surface;

(3) placing the medical material with the anti-adhesion polymer brush-modified surface obtained by step (2) into an azide compound-containing dimethylformamide solution, obtaining a medical material with an azide surface;

(4) placing the medical material with the azide surface prepared in step (3) into an anti-bacterial agent click solution for a click reaction, obtaining an anti-adhesion polymer layer—and anti-bacterial agent layer-comodified anti-bacterial surface.

the oxygen plasma pretreatment in step (1), specifically involves:

performing oxygen plasma pretreatment to the medical material surface, with working parameters of 20-600 W in power, 20-120 Pa in pressure, 2-300 ml/min in gas flow rate, 10° C.-50° C. in temperature, and 2-10 min in time.

conducting chemical graft of amino silane to the medical material surface in step (1), specifically involves:

immersing the pretreated medical material into a solution of amino silane in ethanol for reacting 5-24 h; wherein in the solution of amino silane in ethanol, the volume concentration of the amino silane is 1%-20%, and the temperature is 10° C.-40° C.;

the amino silane is selected from one or more of 3-aminopropyltriethoxysilane, 11-aminoundecyltriethoxysilane, 4-aminobutyltriethoxysilane, N-aminoethyl-aminopropylmethyl dimethoxysilane, N-β-(aminoethyl)-γ-aminopropyltrimethoxysilane.

in step (1), reacting the medical material with the amino silane-grafted surface with an acyl compound, specifically involves:

immersing the medical material with the amino silane-grafted surface into a solution of acyl compounds in dichloromethane for 0.5-24 h; wherein in the solution of acyl compounds in dichloromethane, the volume concentration of the acyl compound is 2%-10%, and the volume concentration of the acid binding agent is 4%-20%;

the acyl compound is selected from one or more of 2-bromoisobutyryl bromide, 2-bromopropionyl bromide, 4-bromobutyl chloride acid, 3-chloropropionyl chloride, 4-chlorovaleryl chloride, and the acid binding agent is selected from one or more of triethylamine, pyridine, and N,N-diisopropylethylamine.

in step (2), placing the medical material with the initiator-modified surface obtained by step (1) into a mixed solution for anti-adhesion monomer radical polymerization for a graft polymerization reaction, specifically involves:

placing the medical material with the initiator-modified surface obtained by step (1) into a mixed solution for atom transfer radical polymerization for a graft polymerization; wherein in the mixed solution, the volume ratio of water to methanol is 1:0.5-1:3, the mass concentration of the anti-adhesion monomer is 2%-20%, the mass concentration of a copper compound is 0.1%-1.2%, the mass concentration of a ligand is 0.3%-3.6%, the reaction time is 0.5-24 h, and the temperature is 10° C.-50° C.;

the anti-adhesion monomer is selected from one or more of acryloyloxyphosphocholine, methacryloxyphosphorylcholine, acrylamidophosphorylcholine, methacrylamidophosphocholine, acryloxysulfonic acid betaine, methacryloxysulfonic acid betaine, acrylamidosulfonic acid betaine, methacrylamidosulfonic acid betaine, acryloxycarboxylic acid betaine, acrylamidocarboxylic acid betaine, methacrylamidocarboxylic acid betaine, vinylpyrrolidone.

in step (3), placing the medical material with the anti-adhesion polymer brush-modified surface obtained by step (2) into an azide compound-containing dimethylformamide solution, obtaining a medical material with an azide surface, specifically involves:

placing the medical material with the anti-adhesion polymer brush-modified surface obtained by step (2) into an azide compound-containing dimethylformamide solution for reacting 4-24 h, obtaining a medical material with an azide surface;

wherein in the azide compound-containing dimethylformamide solution, the mass concentration of the azide compound is 0.5%-5%, and the temperature is 40° C.-80° C.;

the azide compound is selected from one or both of sodium azide and lithium azide.

in step (4), placing the medical material with the azide surface prepared in step (3) into an anti-bacterial agent click solution for a click reaction, specifically involves:

placing the medical material with the azide surface prepared in step (3) into an anti-bacterial agent click solution for a click reaction, wherein the reaction time is 1-5 h, and the reaction temperature is a temperature of 20° C. -50° C.;

in the anti-bacterial agent click solution, the concentration of the anti-bacterial agent is 20-300 µM the concentration of a copper compound is 0.5-5 µM, the concentration of a ligand is 5-50 µM, and the concentration of an ascorbic acid is 25-250 µM; the reaction temperature is 20° C.-50° C., and the time is 1-5 h.

the copper compound is selected from one or more of $CuCl$, $CuSO_4$, $CuCl_2$, $CuBr$ and $CuBr_2$.

the ligand is selected from one or more of 2,2'-bipyridine, tetramethylethylenediamine, pentamethyldiethylenetriamine, hexamethyltriethylenetetramine, tris(N,N-dimethylaminoethyl)amine, N,N,N',N'',N''-pentamethyldivinyltriamine and tris[2-(dimethylamino)ethyl]amine.

the anti-bacterial agent is an anti-bacterial polypeptide with a sequence of Pra-Lys-Arg-Trp-Trp-Lys-Trp-Trp-Arg-Arg (SEQ. ID NO: 3) or Pra-Arg-Arg-Trp-Trp-Lys-Trp-Trp-Arg-Lys (SEQ ID NO: 4).

Compared with the prior art, the present invention has the following advantages and beneficial effects:

The present invention relates to preparing a double-layered bifunctional anti-bacterial surface on a material surface with an anti-adhesion polymer as a bottom layer and an anti-bacterial agent as a upper layer by introducing an atom transfer radical polymerization initiator on the medical material surface, which comprises firstly conducting graft of an anti-adhesion polymer, then introducing an azide group, and finally introducing an anti-bacterial agent by a click reaction. Since the anti-adhesion polymer and the anti-bacterial agent are located in different graft layers, not only the mutual interference of performance is avoided, but also the problem that the anti-bacterial agent is degraded by the enzyme in the body is improved. The synergistic action of the anti-adhesion polymer and the anti-bacterial agent imparts more excellent long-acting anti-bacterial performance to the surface, and reduces the adverse effects of the bactericidal layer on blood and body cells, obtaining excellent biocompatibility. The present invention solves the problem of nosocomial infections caused by medical devices.

DETAILED DESCRIPTION OF EMBODIMENTS

The present invention will be further described in detail in conjunction with embodiments below, but the implementations of the present invention are not limited thereto.

Example 1

Figure 1:
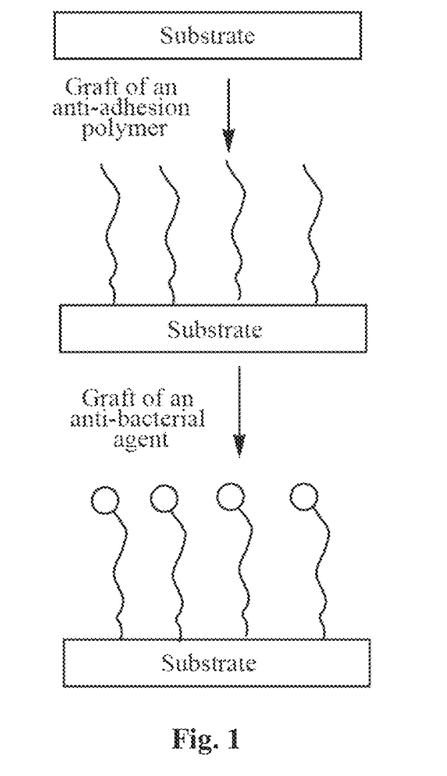
FIG. 1 shows a schematic view of the process of the method for preparing an anti-bacterial surface on a silicon wafer surface according to example 1 of the present invention.

As shown in FIG. 1, the method for preparing an anti-bacterial surface on a silicon wafer surface of this example comprises the steps of:

(1) performing oxygen plasma pretreatment to the silicon substrate surface, with working parameters of 100 W in power, 20 Pa in pressure, 300 ml/min in gas flow rate, 30° C. in temperature, and 5 min in time; immersing the pre-treated silicon substrate into an solution of 3-aminopropyltriethoxysilane in ethanol, and conducting chemical graft of amino silane on the silicon substrate surface with a reaction temperature of 30° C. for 5 h; wherein the volume concentration of 3-aminopropyltriethoxysilane is 2%;

(2) immersing the silicon substrate with an amino silane-grafted surface into a solution of acyl compounds in dichloromethane for reacting with the acyl compounds at a temperature of 20° C. for 3 h, obtaining a silicon substrate surface with an initiator-modified surface for atom transfer radical polymerization; wherein in the solution of acyl compounds in dichloromethane, the volume concentration of 2-bromoisobutyryl bromide is 2%, and the volume concentration of triethylamine is 4%;

(3) placing the silicon substrate with an initiator-modified surface into a mixed solution for atom transfer radical polymerization for a graft polymerization reaction for 2 h at a temperature of 25° C., obtaining a silicon substrate surface with an anti-adhesion polymer brush-modified surface; the volume ratio of water to methanol in the mixed solution is 1:1, the mass concentration of the methacryloxysulfonic acid betaine monomer aqueous solution in the mixed solution is 5%, and the mass concentration of copper bromide is 0.3%, and the mass concentration of 2,2'-bipyridine is 0.9%;

(4) placing the silicon substrate with an anti-adhesion polymer brush-modified surface into an azide compound-containing dimethylformamide solution, obtaining a silicon substrate with an azide surface; the reaction conditions for azidation involves in the azide compound-containing dimethylformamide solution, the mass concentration of sodium azide is 5%, the temperature is 40° C., and the time is 8 h, obtaining a anti-adhesion polymer-modified surface with terminal-azide;

(5) after washing, placing the medical material with an azide surface into a click solution of an anti-bacterial agent (with a sequence of Pra-Lys-Arg-Trp-Trp-Lys-Trp-Trp-Arg-Arg SEQ. ID. NO: 3)) for a click reaction performed at a temperature of 37° C. and for 2 h, obtaining an anti-adhesion polymer brush bottom layer- and an anti-bacterial agent upper layer-comodified double-layered anti-bacterial surface; in the click solution, the concentration of the anti-bacterial agent is 100 μM, the concentration of copper sulfate is 1 μM, the concentration of the ligand tris[2-(dimethylamino)ethyl]amine is 10 μM, and the concentration of sodium ascorbate is 50 μM.

Figure 2:
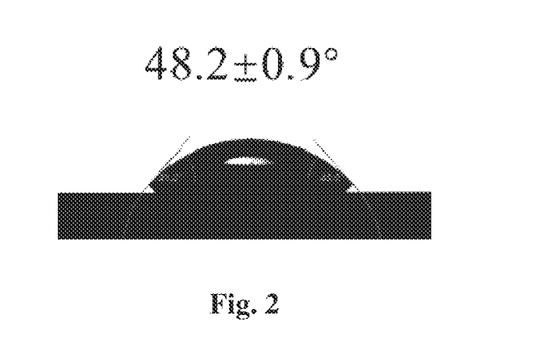
FIG. 2 shows a water contact angle of the surface of the untreated silicon substrate.
Figure 3:
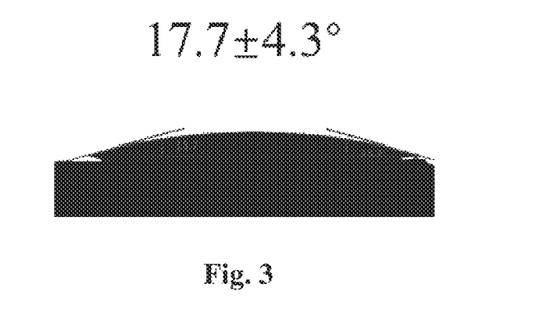
FIG. 3 shows a water contact angle of the surface of the silicon substrate with an anti-adhesion polymer brush-modified surface obtained in step (3) of example 1 of the present invention.
Figure 4:
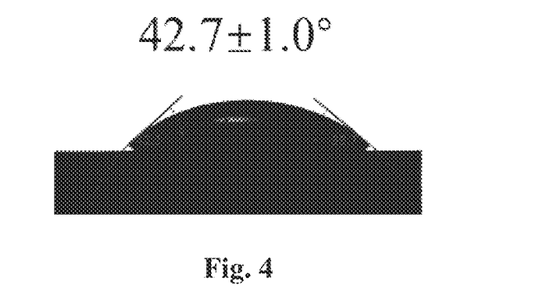
FIG. 4 shows a water contact angle of the anti-adhesion polymer brush bottom layer- and the anti-bacterial agent upper layer-comodified double-layered anti-bacterial surface prepared in example 1 of the present invention.

The water contact angle of the surface of the untreated silicon substrate is as shown in FIG. 2. The water contact angle of the surface of the silicon substrate with an anti-adhesion polymer brush-modified surface obtained in step (3) of this example is as shown in FIG. 3. The water contact angle of the anti-adhesion polymer brush bottom layer- and the anti-bacterial agent upper layer-comodified double-layered anti-bacterial surface prepared in this example is as shown in FIG. 4. It can be seen from FIGS. 2 to 4 that the contact angle after the treatment in each step has a significant change, indicating successful graft of the anti-adhesion polymer and the anti-bacterial agent.

Figure 5:
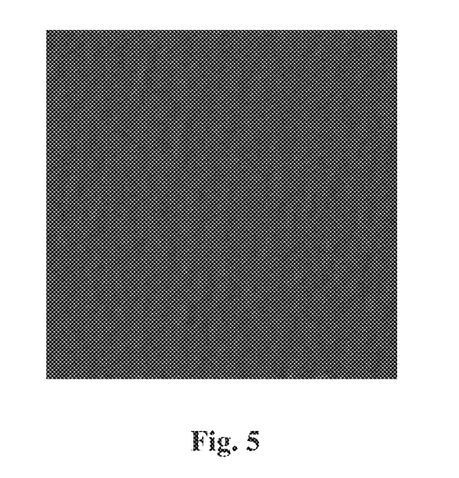
FIG. 5 shows a surface topography of the surface of the untreated silicon substrate.
Figure 6:
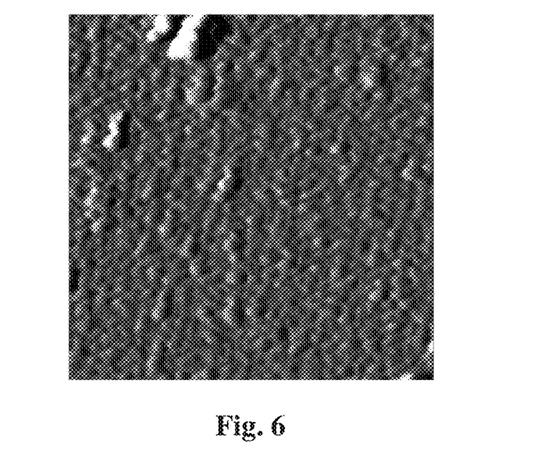
FIG. 6 shows a surface topography of the anti-adhesion polymer brush bottom layer- and the anti-bacterial agent upper layer-comodified double-layered anti-bacterial surface prepared in example 1 of the present invention.

The surface topography of the surface of the untreated silicon substrate is as shown in FIG. 5. The surface topography of the anti-adhesion polymer brush bottom layer- and the anti-bacterial agent upper layer-comodified double-layered anti-bacterial surface prepared in this example is as shown in FIG. 6. It can be seen from FIGS. 5 to 6 that the surface topography after the treatment in each step has a significant change, indicating successful graft of the anti-adhesion polymer and the anti-bacterial agent.

Figure 7:
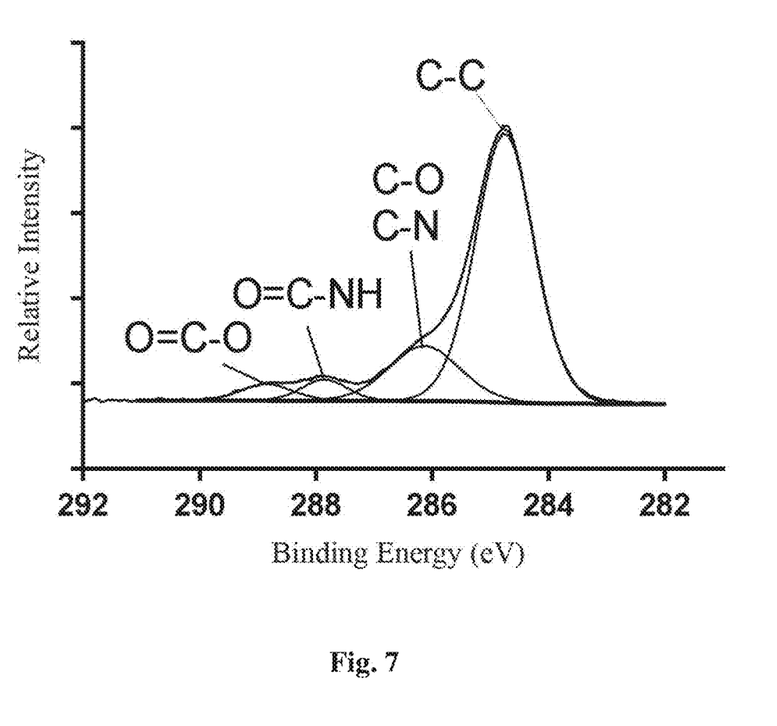
FIG. 7 shows a peak separation of C element in X-ray photoelectron spectroscopy of an anti-adhesion polymer brush bottom layer- and an anti-bacterial agent upper layer-comodified double-layered anti-bacterial surface prepared in example 1 of the present invention.
Figure 8:
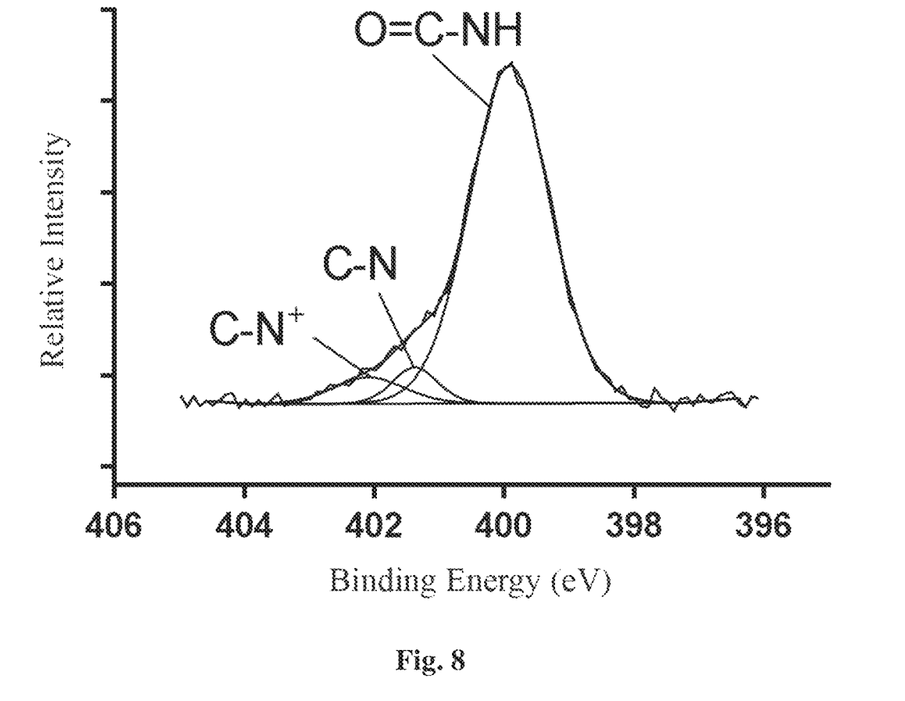
FIG. 8 shows a peak separation of N element in X-ray photoelectron spectroscopy of an anti-adhesion polymer brush bottom layer—and an anti-bacterial agent upper layer-comodified double-layered anti-bacterial surface prepared in example 1 of the present invention.

The peak separation of C element in X-ray photoelectron spectroscopy of the anti-adhesion polymer brush bottom layer—and the anti-bacterial agent upper layer-comodified double-layered anti-bacterial surface prepared in this example is as shown in FIG. 7, and the peak separation of N element of same is as shown in FIG. 8. It can be seen that both the anti-adhesion polymer and the anti-bacterial agent are successfully grafted to the surface.

Figure 9:
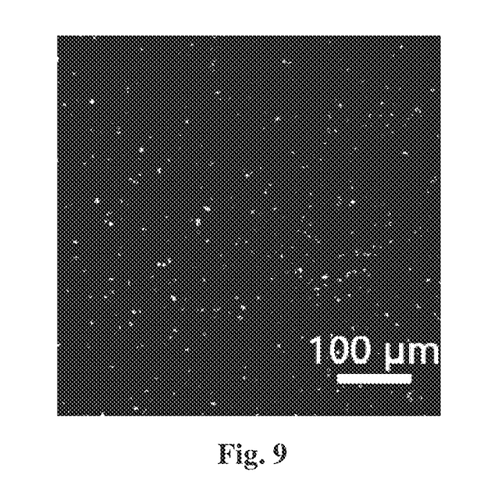
FIG. 9 shows the bacterial growth of $10^6$ CFU/ml bacteria after incubation on the surface of the untreated silicon substrate for 2.5 hours.
Figure 10:
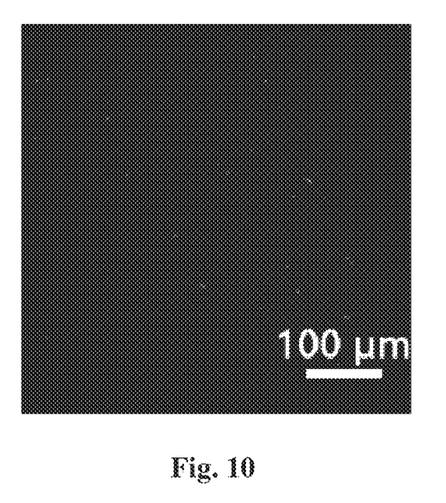
FIG. 10 shows the bacterial growth of $10^6$ CFU/ml bacteria after incubation on the anti-adhesion polymer brush bottom layer—and the anti-bacterial agent upper layer-comodified double-layered anti-bacterial surface prepared in example 1 of the present invention for 2.5 hours.

The bacterial growth of $10^6$ CFU/ml bacteria after incubation on the surface of the untreated silicon substrate and on the anti-adhesion polymer brush bottom layer- and the anti-bacterial agent upper layer-comodified double-layered anti-bacterial surface prepared in this example for 2.5 hours is as shown in FIG. 9 and FIG. 10 respectively.

Figure 11:
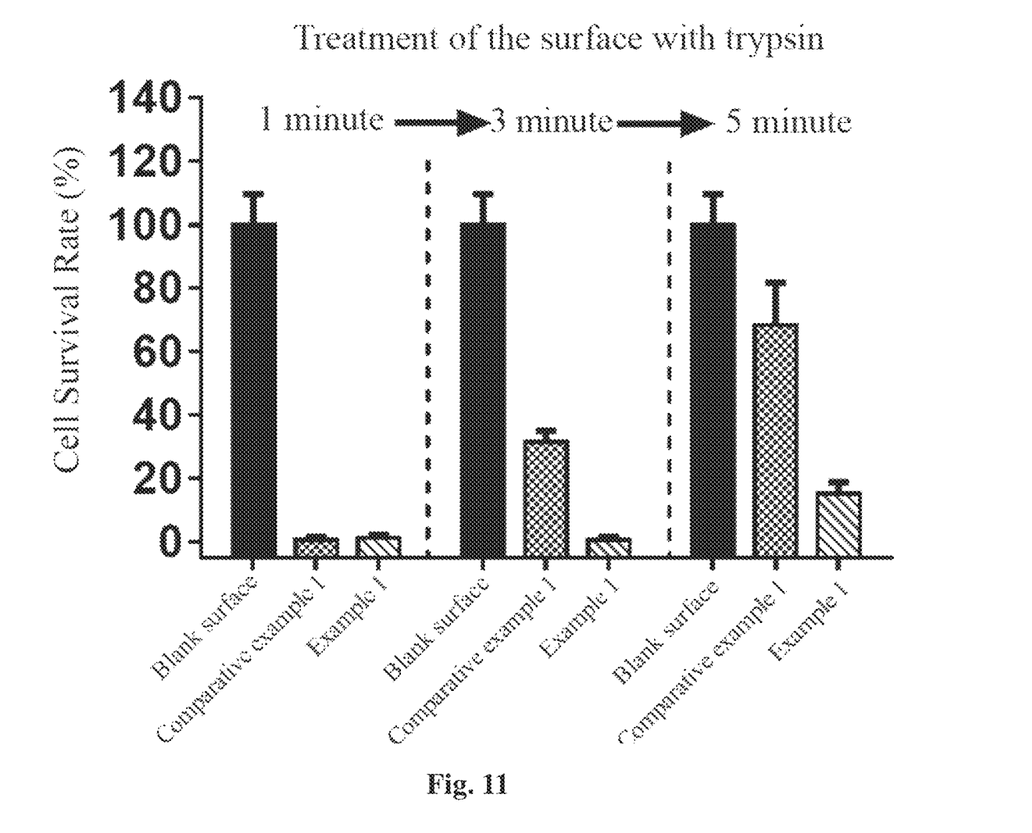
FIG. 11 shows the anti-bacterial performance of the surface of samples of comparative example 1 and example 1 after treatment with 1 mg/ml trypsin for 1, 3, and 5 minutes.

After the anti-adhesion polymer brush bottom layer—and an anti-bacterial agent upper layer-comodified double-layered anti-bacterial surface prepared in this example is treated with 1 mg/ml trypsin for 1, 3, and 5 minutes, the anti-bacterial performance of the surface is as shown in FIG. 11.

Comparative Example 1

This comparative example is the same as example 1 except that step (3) is not carried out.

Figure 12:
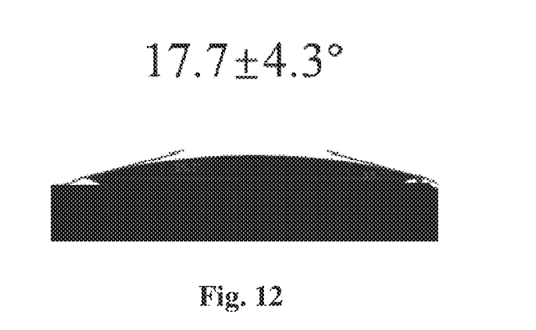
FIG. 12 shows a water contact angle of the surface of the sample prepared in comparative example 1.
Figure 13:
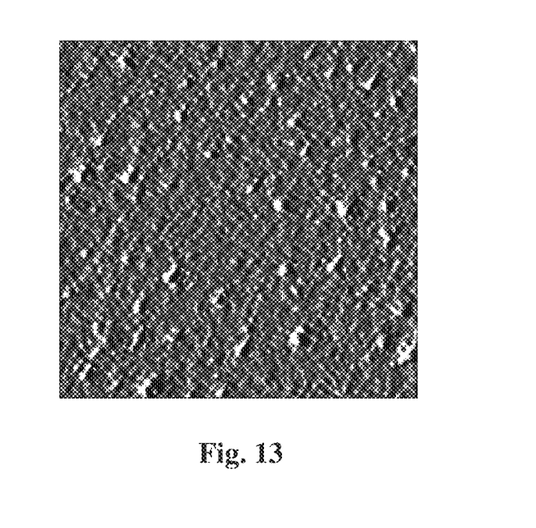
FIG. 13 shows a surface topography of the surface of the sample prepared in comparative example 1.
Figure 14:
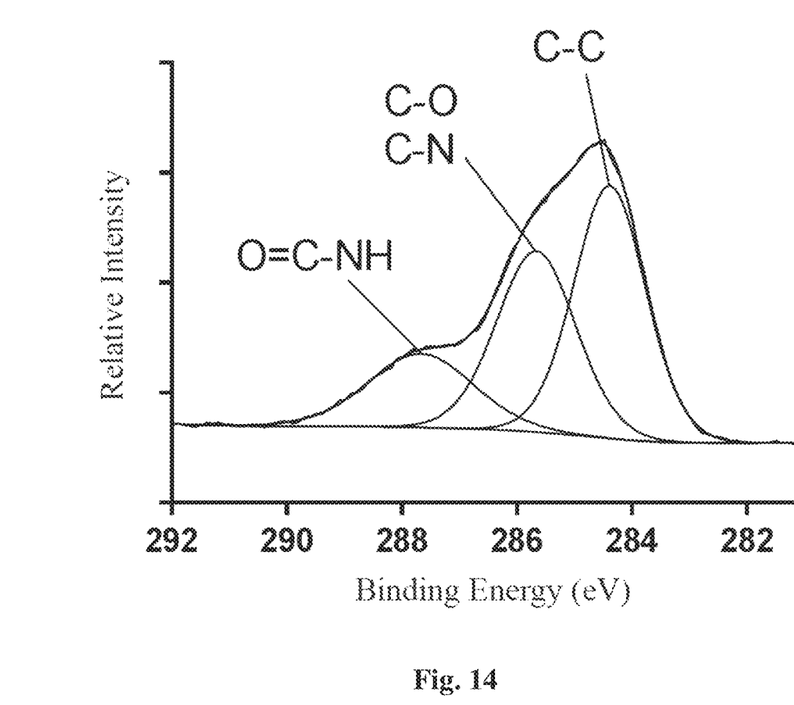
FIG. 14 shows a peak separation of C element in X-ray photoelectron spectroscopy of the surface of the sample prepared in comparative example 1.
Figure 15:
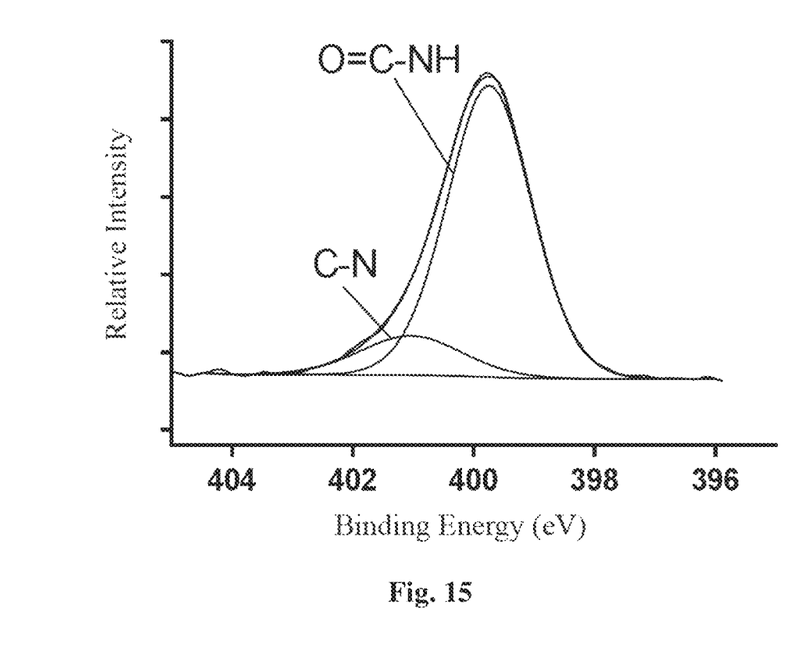
FIG. 15 shows a peak separation of N element in X-ray photoelectron spectroscopy of the surface of the sample prepared in comparative example 1.

The water contact angle of the surface of the sample prepared in this comparative example is as shown in FIG. 12, and the surface morphology of same is as shown in FIG. 13. The anti-bacterial performance of the surface after treatment with 1 mg/ml trypsin for 1, 3, 5 minutes is as shown in FIG. 11. The peak separation of C element in X-ray photoelectron spectroscopy is as shown in FIG. 14, and the peak separation of N element is as shown in FIG. 15.

It can be seen from the example and comparative example 1 that the anti-bacterial agent is successfully grafted to the surface, but the amount of the anti-bacterial agent grafted in the example is smaller than that in comparative example 1, wherein the example shows better anti-bacterial performance and also a better anti-enzymatic hydrolysis ability.

Example 2

The method for preparing an anti-bacterial surface on a medical titanium surface of this example comprises the steps of:

(1) performing oxygen plasma pretreatment to the medical titanium surface, with working parameters of 50 W in power, 30 Pa in pressure, 30 ml/min in gas flow rate, 30° C. in temperature, and 3 min in time; immersing the pretreated medical titanium surface into an solution of 3-aminopropyltriethoxysilane in ethanol, and conducting graft of amino silane on the medical titanium surface with a reaction condition of 8% in volume concentration of 3-aminopropyltriethoxysilane, 25° C. in temperature and 1 h in time;

(2) immersing the medical titanium with an amino silane-grafted surface into a solution of acyl compounds in dichloromethane for reacting with the acyl compounds, obtaining a silicon substrate surface with an initiator-modified surface for atom transfer radical polymerization; where the reaction conditions involves: the volume concentration of 2-bromopropionyl bromide is 8%, the volume concentration of triethylamine is 16%, the temperature is 20° C., and the time is 1 h;

(3) placing the medical titanium with an initiator-modified surface into a mixed solution for atom transfer radical polymerization for a graft polymerization at a temperature of 37° C. for 0.5 h, wherein the mixed solution contains water and methanal at a volume ratio of 1:0.5, methacrylamidocarboxylic acid betaine monomer aqueous solution at a mass concentration of 10%, copper bromide at a mass concentration of 0.6%, and 2,2'-bipyridine at a mass concentration of 1.8%; the reaction conditions for azidation involves in the azide compound-containing dimethylformamide solution, the mass concentration of sodium azide is 2%, the temperature is 70° C., and the time is 8 h, obtaining a anti-adhesion polymer-modified surface with terminal-azide;

(4) after washing, placing the medical material with an azide surface into a click solution of an anti-bacterial agent (Pra-Arg-Arg-Trp-Trp-Lys-Trp-Trp-Arg-Lys (SEQ ID NO: 4) for a click reaction performed at a temperature of 25° C. and for 4 h, wherein the concentration of the anti-bacterial agent is 200 μM, the concentration of sodium chloride is 2 μM, the concentration of ligand pentamethyldiethylenetriamine is 20 μM, and the concentration of ascorbic acid is 100 μM, obtaining an anti-adhesion polymer brush bottom layer- and an anti-bacterial agent upper layer-comodified double-layered anti-bacterial surface.

The test results of the anti-adhesion polymer brush bottom layer- and the anti-bacterial agent upper layer-comodified double-layered anti-bacterial surface prepared in this example are similar to those in example 1, which will not be described again herein.

Example 3

The method for preparing an anti-bacterial surface on a medical titanium surface of this example comprises the steps of:

(1) performing oxygen plasma pretreatment to the medical titanium surface, with working parameters of 400 W in power, 60 Pa in pressure, 250 ml/min in gas flow rate, 30° C. in temperature, and 10 min in time; immersing the pretreated medical titanium surface into an solution of 3-aminopropyltriethoxysilane in ethanol, and conducting graft of amino silane on the medical titanium surface with a reaction condition of 8% in volume concentration of 3-aminopropyltriethoxysilane, 25° C. in temperature and 0.5 h in time;

(2) immersing the medical titanium with an amino silane-grafted surface into a solution of acyl compounds for reacting with the acyl compounds, obtaining a silicon substrate surface with an initiator-modified surface for atom transfer radical polymerization; the reaction conditions are: the volume concentration of 2-bromoisobutyryl bromide is 8%, the volume concentration of triethylamine is 16%, the temperature is 25° C., and the time is 0.5 h;

(3) placing the medical titanium with an initiator-modified surface into a mixed solution for atom transfer radical polymerization for a graft polymerization at a temperature of 20° C. for 18 h, wherein the mixed solution contains water and methanol at a volume ratio of 1:3, acryloxycarboxylic acid betaine monomer at a mass concentration of 2%, copper bromide at a mass concentration of 0.2%, and 2,2'-bipyridine at a mass concentration of 0.6%; the reaction conditions for azidation involves in the azide compound-containing dimethylformamide solution, the mass concentration of lithium azide is 1%, the temperature is 50° C., and the time is 18 h, obtaining an anti-adhesion polymer-modified surface with terminal-azide.

(4) after washing, placing the medical material with an azide surface into a click solution of an anti-bacterial agent for a click reaction performed at a temperature of 37° C. for 3 h, wherein the concentration of the anti-bacterial agent is 50 μM, the concentration of copper sulfate is 1 μM, the concentration of ligand tris[2-(dimethylamino)ethyl]amine is 10 μM, and the concentration of ascorbic acid is 50 μM, obtaining an anti-adhesion polymer brush bottom layer- and an anti-bacterial agent upper layer-comodified double-layered anti-bacterial surface.

The test results of the anti-adhesion polymer brush bottom layer- and the anti-bacterial agent upper layer-comodified double-layered anti-bacterial surface prepared in this example are similar to those in example 1, which will not be described again herein.

The amino silane of the present invention can also be selected from one or more of 3-aminopropyltriethoxysilane, 11-aminoundecyltriethoxysilane, 4-aminobutyltriethoxysilane, N-aminoethyl-aminopropylmethyl dimethoxysilane, N-β-(aminoethyl)-γ-aminopropyltrimethoxysilane.

The acyl compound of the present invention can also be selected from one or more of 2-bromoisobutyryl bromide, 2-bromopropionyl bromide, 4-bromobutyl chloride acid, 3-chloropropionyl chloride, 4-chlorovaleryl chloride, and the acid binding agent is selected from one or more of triethylamine, pyridine, and N,N-diisopropylethylamine.

The anti-adhesion monomer of the present invention can also be selected from one or more of acryloyloxyphosphocholine, methacryloxyphosphorylcholine, acrylamidophosphorylcholine, methacrylamidophosphocholine, acryloxysulfonic acid betaine, methacryloxysulfonic acid betaine, acrylamidosulfonic acid betaine, methacrylamidosulfonic acid betaine, acryloxycarboxylic acid betaine, acrylamidocarboxylic acid betaine, methacrylamidocarboxylic acid betaine, vinylpyrrolidone.

The copper compound of the present invention can also be selected from one or more of CuCl, $CuSO_4$, $CuCl_2$, CuBr and $CuBr_2$.

The ligand of the present invention can also be selected one or more of 2,2'-bipyridine, tetramethylethylenediamine, pentamethyldiethylenetriamine, hexamethyltriethylenetramine, tris(N,N-dimethylaminoethyl)amine, N,N,N',N'',N''-pentamethyldivinyltriamine and tris[2-(dimethylamino)ethyl]amine.

The foregoing embodiments are preferred implementations of the present invention. However, the implementations of the present invention are not limited to the described embodiments. Any other changes, modifications, replacements, combinations, and simplifications made without departing from the spirit, essence, and principle of the present invention shall all be equivalent replacements, and all fall within the protection scope of the present invention.

The invention claimed is:

1. A method for preparing an anti-bacterial surface on a medical material surface, comprising:
   (1) conducting chemical graft of amino silane after performing oxygen plasma pretreatment to the medical material surface and then reacting the medical material with an amino silane-grafted surface with an acyl compound, obtaining a medical material with an initiator-modified surface for atom transfer radical polymerization;
   (2) placing the medical material with the initiator-modified surface obtained by step (1) into an mixed solution for anti-adhesion monomer radical polymerization for a graft polymerization reaction, obtaining a medical material with an anti-adhesion polymer brush-modified surface;
   (3) placing the medical material with the anti-adhesion polymer brush-modified surface obtained by step (2) into an azide compound-containing dimethylformamide solution, obtaining a medical material with an azide surface;
   (4) placing the medical material with the azide surface prepared in step (3) into an anti-bacterial agent click solution for a click reaction, obtaining an anti-adhesion polymer layer- and anti-bacterial agent layer-comodified anti-bacterial surface.

2. The method for preparing an anti-bacterial surface on a medical material surface according to claim 1, wherein the oxygen plasma pretreatment in step (1) comprises:
   performing oxygen plasma pretreatment to the medical material surface, with working parameters of 20-600 W in power, 20-120 Pa in pressure, 2-300 ml/min in gas flow rate, 10° C.-50° C. in temperature, and 2-10 min in time.

3. The method for preparing an anti-bacterial surface on a medical material surface according to claim 1, wherein conducting the chemical graft of amino silane to the medical material surface in step (1) comprises:
   immersing the pretreated medical material into a solution of amino silane in ethanol for reacting 5-24 h; wherein in the solution of amino silane in ethanol, the volume concentration of the amino silane is 1%-20%, and the temperature is 10° C.-40° C.;
   the amino silane is selected from one or more of 3-aminopropyltriethoxysilane, 11-aminoundecyltriethoxysilane, 4-aminobutyltriethoxysilane, N-aminoethyl-aminopropylmethyl dimethoxysilane, or N-β-(aminoethyl)-γ-aminopropyltrimethoxysilane.

4. The method for preparing an anti-bacterial surface on a medical material surface according to claim 1, wherein in step (1), reacting the medical material with the amino-silane grafted surface with an acyl compound comprises:
   immersing the medical material with the amino silane-grafted surface into a solution of acyl compounds in dichloromethane for 0.5-24 h; wherein in the solution of acyl compounds in dichloromethane, the volume concentration of the acyl compound is 2%-10%, and the volume concentration of the acid binding agent is 4%-20%;
   the acyl compound is selected from one or more of 2-bromoisobutyryl bromide, 2-bromopropionyl bromide, 4-bromobutyl chloride acid, 3-chloropropionyl chloride, or 4-chlorovaleryl chloride, and the acid binding agent is selected from one or more of triethylamine, pyridine, or N,N-diisopropylethylamine.

5. The method for preparing an anti-bacterial surface on a medical material surface according to claim 1, wherein in step (2), placing the medical material with the initiator-modified surface obtained by step (1) into a mixed solution for anti-adhesion monomer radical polymerization for a graft polymerization reaction comprises:
   placing the medical material with the initiator-modified surface obtained by step (1) into a mixed solution for atom transfer radical polymerization for a graft polymerization; wherein in the mixed solution, the volume ratio of water to methanol is 1:0.5-1:3, the mass concentration of the anti-adhesion monomer is 2%-20%, the mass concentration of a copper compound is 0.1%-1.2%, the mass concentration of a ligand is 0.3%-3.6%, the reaction time is 0.5-24 h, and the temperature is 10° C.-50° C.;
   the anti-adhesion monomer is selected from one or more of acryloyloxyphosphocholine, methacryloxyphosphorylcholine, acrylamidophosphorylcholine, methacrylamidophosphocholine, acryloxysulfonic acid betaine, methacryloxysulfonic acid betaine, acrylamidosulfonic acid betaine, methacrylamidosulfonic acid betaine, acryloxycarboxylic acid betaine, acrylamidocarboxylic acid betaine, methacrylamidocarboxylic acid betaine, or vinylpyrrolidone.

6. The method for preparing an anti-bacterial surface on a medical material surface according to claim 1, wherein in step (3), placing the medical material with the anti-adhesion polymer brush-modified surface obtained by step (2) into an azide compound-containing dimethylformamide solution, obtaining a medical material with an azide surface comprises:
   placing the medical material with the anti-adhesion polymer brush-modified surface obtained by step (2) into an azide compound-containing dimethylformamide solution for reacting 4-24 h, obtaining a medical material with an azide surface;
   wherein in the azide compound-containing dimethylformamide solution, the mass concentration of the azide compound is 0.5%-5%, and the temperature is 40° C.-80° C.;
   the azide compound is selected from one or both of sodium azide and lithium azide.

7. The method for preparing an anti-bacterial surface on a medical material surface according to claim 1, wherein in step (4), placing the medical material with the azide surface prepared in step (3) into an anti-bacterial agent click solution for a click reaction comprises:
   placing the medical material with the azide surface prepared in step (3) into an anti-bacterial agent click solution for a click reaction, wherein the reaction time is 1-5 h, and the reaction temperature is a temperature of 20° C.-50° C.;
   in the anti-bacterial agent click solution, the concentration of the anti-bacterial agent is 20-300 μM, the concentration of a copper compound is 0.5-5 μM, the concentration of a ligand is 5-50 μM, and the concentration of an ascorbic acid is 25-250 μM; the reaction temperature is 20° C.-50° C., and the time is 1-5 h.

8. The method for preparing an anti-bacterial surface on a medical material surface according to claim 7, wherein the copper compound is selected from one or more of CuCl, $CuSO_4$, $CuCl_2$, CuBr or $CuBr_2$.

9. The method for preparing an anti-bacterial surface on a medical material surface according to claim 7, wherein the ligand is selected from one or more of 2,2'-bipyridine, tetramethylethylenediamine, pentamethyldiethylenetriamine, hexamethyltriethylenetetramine, tris(N,N-dimethylaminoethyl)amine, or N,N,N',N'',N''-pentamethyldivinyltriamine and tris[2-(dimethylamino)ethyl]amine.

10. The method for preparing an anti-bacterial surface on a medical material surface according to claim 7, wherein the anti-bacterial agent is an anti-bacterial polypeptide with a sequence of Pra-Lys-Arg-Trp-Trp-Lys-Trp-Trp-Arg-Arg (SEQ ID NO: 3) or Pra-Arg-Arg-Trp-Trp-Lys-Trp-Trp-Arg-Lys (SEQ ID NO: 4).

* * * * *

UNITED STATES PATENT AND TRADEMARK OFFICE
CERTIFICATE OF CORRECTION

| | | |
|---|---|---|
| PATENT NO. | : 11,426,496 B2 | Page 1 of 1 |
| APPLICATION NO. | : 16/475196 | |
| DATED | : August 30, 2022 | |
| INVENTOR(S) | : Li Ren et al. | |

It is certified that error appears in the above-identified patent and that said Letters Patent is hereby corrected as shown below:

On the Title Page

Item [73], Line 1, after "Technology" insert -- , (CN) --

Signed and Sealed this
Fifteenth Day of November, 2022

*Katherine Kelly Vidal*
Katherine Kelly Vidal
*Director of the United States Patent and Trademark Office*